United States Patent [19]

Walker

[11] Patent Number: 4,795,475

[45] Date of Patent: Jan. 3, 1989

[54] PROSTHESIS UTILIZING SALT-FORMING OXYACIDS FOR BONE FIXATION

[76] Inventor: Michael M. Walker, 5100 DuPont Boulevard, Ft. Lauderdale, Fla. 33308

[21] Appl. No.: 764,102

[22] Filed: Aug. 9, 1985

[51] Int. Cl.$^4$ ................................................ A61F 2/54
[52] U.S. Cl. ................................. 623/66; 128/92 YQ; 427/2; 433/201.1; 106/287.23; 623/11; 623/16
[58] Field of Search .................. 427/2; 623/11, 16, 66; 128/92 R, 92 G, 920 V, 92 YR, 92 YQ, 92 YG; 433/201, 191, 195; 106/287.23, 287.24, 287.26

[56] References Cited

U.S. PATENT DOCUMENTS

| | | |
|---|---|---|
| 3,787,900 | 1/1974 | McGee . |
| 3,789,029 | 1/1974 | Hodosh .................... 623/16 |
| 3,919,723 | 11/1975 | Heimke et al. . |
| 3,986,212 | 10/1976 | Sauer ..................... 128/92 YG |
| 3,987,497 | 10/1976 | Stoy et al. ................... 623/13 |
| 4,091,201 | 5/1978 | Argoudelis et al. ........... 536/17 |
| 4,093,576 | 6/1978 | de Wijn ...................... 623/16 |
| 4,164,794 | 8/1979 | Spector et al. ............ 128/92 YG |
| 4,168,326 | 9/1979 | Broemer et al. . |
| 4,330,514 | 5/1982 | Nagai et al. . |
| 4,348,329 | 9/1982 | Chapman .................... 260/403 |
| 4,366,183 | 12/1982 | Ghommidh et al. . |
| 4,373,217 | 2/1983 | Draenert . |
| 4,377,010 | 3/1983 | Fydelor ................... 128/92 C |
| 4,437,192 | 3/1984 | Fujiu et al. . |

FOREIGN PATENT DOCUMENTS

| | | | |
|---|---|---|---|
| 0154114 | 9/1982 | Japan ......................... 623/66 |
| 57-143372 | 9/1982 | Japan ......................... 623/16 |

OTHER PUBLICATIONS

Sauer; "The Role of Porous Polymeric Materials in Prosthetic Attachment"; The Fifth Annual Biomaterials Symposium; Apr. 1973; Clemson University.
L. L. Hench, R. J. Splinter, W. C. Allen, T. K. Greenlee, *J. Biomed. Mater. Res. Symp.* 2, 117 (1972).
L. L. Hench and H. A. Paschall, *J. Biomed. Mater. Res. Symp,* 4, 25 (1973).
J. C. McNeur, *The Medical Journal of Australia,* 542, Nov. 15, 1980.
L. L. Hench, *Science,* 208, 826 (1980).
Michael M. Walker and J. Lawrence Katz, *Bulletin of the Hospital for Joint Diseases Orthopaedic Institute,* vol. XLIII, No. 2, 103 (1983).
J. Lawrence Katz and Ivan C. Mow, *Biomat., Med. Dev., Art. Org.,* 1(4), 575–634 (1973).
C. A. Homsy, *Orthopedic Clinic of North America,* vol. 4, No. 2, Apr. 1973.
M. Spector, W. F. Flemming, A. Kreutner and B. W. Sauer, *J. Biomed. Mater. Res. Symp.,* 7, 595 (1976).
H. J. Cestero, Jr., K. E. Salyer and I. R. Toranto, *J. Biomed. Mater. Res. Symp.,* 6, 1 (1975).
B. W. Sauer, et al., *J. Biomed. Mater. Res. Symp.,* 5 (Part I), 145 (1974).
M. Spector, M. J. Michno, W. H. Smarook and G. T. Kwiatkowski, *J. Biomed. Mater. Res. Symp.,* 12, 665 (1978).
D. C. Smith, "A Review of the Zinc Polycarboxylate Cements", *Journal of the Canadian Dental Association,* No. 1, 1971.

*Primary Examiner*—Richard J. Apley
*Assistant Examiner*—Paul Prebilic

[57] ABSTRACT

An improved orthopedic or dental implant is formed so that at least its bone contacting surfaces are comprised of a biocompatible organic polymer substituted with salt-forming sulfur oxyacid groups or biocompatible salts thereof. In addition, a method of promoting bone tissue deposition and adhesion has been found which utilizes an implant having a biocompatible organic polymer substituted with carbon, sulfur or phosphorous oxyacid groups or sales thereof on its bone contacting surfaces. Such oxyacid substituted polymers have been found to promote interfacial osteogenesis, to enhance the rate of bony growth into porous implant surfaces, and to foster direct chemical bonding of the implant surface with the biological polymers present in developing bone tissue.

29 Claims, No Drawings

PROSTHESIS UTILIZING SALT-FORMING FOR BONE FIXATION

BACKGROUND AND SUMMARY OF THE INVENTION

This invention relates to a surgical implant adapted for secure attachment to living bone. More particularly this invention relates to an improved orthopedic or dental implant formed to have bone contacting surfaces comprised of biocompatible organic polymers substituted with oxyacid groups or salts thereof. Applicant has found that the presence of such oxyacid substituted polymers, at least at the bone contacting surface, promotes interfacial osteogenesis and provides sites to which bone can chemically bond, thus fostering direct chemical bonding of the implant surface with the biological polymers present in developing bone tissue.

In severe cases of arthritis or other bone and joint degenerative diseases, surgical replacement of the affected joint and bone tissue is a commonly used procedure. In cases of dentition lost to disease or trauma, endosseous dental implants have been used to restore function. Research and development efforts have been highly successful in identifying materials for use alone or as composite structures for prosthetic implants —materials which meet both the basic physical (biomechanical) demands and the chemical biocompatibility requirements dictated by their use in implanted devices. Due to the stringent mechanical demands placed on load bearing bone prostheses, metals have been the material of choice for the most severely loaded parts of such implants. The metals generally used in load bearing components of orthopedic devices are limited to the cobalt, chromium, molybdenum alloys, titanium and surgical stainless steel. More recently, high strength ceramics and reinforced polymers have been introduced for such applications.

Notwithstanding the major advances which have been made in implant materials development, patients still face the trauma and expense of implant failure. The most common point of bone implant failure is not breakage or failure of the prosthetic implant itself; the more common failure of implants is at the living bone-implant interface. In other words, the implant simply works loose from its implanted position. Early total joint replacements were fixed to the bone of a recipient through a press fit of the prosthesis into a carefully prepared surgical bed. This method often resulted in loosening of the implant in the long term.

A review of the recent literature reveals significant research and development efforts directed to improving implant-bone fixation. A major advance in joint replacement surgery was the introduction of the use of poly(methyl methacrylate) [PMMA] bone cement for fixing the components of a joint prosthesis to bone. PMMA is not a glue or adhesive but a true cement which works mechanically. It is applied in a dough-like state as a grouting agent between the bone and the implant so that it can flow around the contours of the bone and the implant and into the interstices of cancellous bone. Upon hardening it forms a mechanically interlocked attachment between the bone and the implant. While PMMA bone cement provides a secure fixation of the prosthesis with living bone in the short term, the long term loss of implant fixation has proven to be a significant problem. The degeneration in implant fixation begins with a resorption of the bony tissue immediately adjacent to the bone cement and the replacement of that tissue with a soft fibrous tissue capsule. Since the fibrous tissue is far more compliant than bone, the thicker the capsule the looser the implant becomes. Since the thickness of the capsule tends to increase with motion the loosening process is self-reinforcing.

In an alternative method of implant fixation enjoying widespread use, the implant is provided with a highly porous surface coating that provides interstices into which bone can grow. Materials which provide pore size distributions of 50 to 500 microns have shown considerable promise and have become more widely used especially in young, active patients. For bone to interlock with the pore structure of the implant the implant must be firmly fixed at the time of surgery and load application must be minimized during the in growth period. Immediate surgical fixation is usually accomplished by the mechanical impaction of the implant into a slightly sub-sized surgical bed. The problems related to both of these fixation methods arise from the lack of affinity demonstrated by healing bone for the heretofore known metallic alloys and polymeric materials used in reconstructive orthopedic and oral surgery. When these materials are placed into bony defects, bone does not deposit directly onto the implant surfaces but, significantly, remains separated from them by at least a thin layer of soft tissue. This precludes the possibility of any chemical bond between the bone and the implant and limits the fixation modes to those based on mechanical interlock. Materials of this type are defined as "osteophobic" for the purposes of this disclosure.

Due to the problem of obtaining fixation to living bone by purely mechanical means, more recent research efforts have been directed at finding more bone-tissue-compatible implant materials, particularly materials having some demonstrable chemical affinity for regenerating bone tissue. It has been found that when certain minerals are implarted into osseous defects, newly forming bone will deposit directly onto the mineral surface without any intervening layer of soft tissue. Furthermore not only does bone deposit directly on the surface of these minerals, but it has been observed that bone will adhere even to a smooth surface of said minerals through the formation of chemical bonds across the bone-mineral implant surface.

For the purposes of this disclosure materials onto which bone deposits and chemically bonds are defined as "osteophilic", and the process whereby bone deposits directly onto a free surface is defined as "interfacial osteogenesis." The first materials recognized to have osteophilic properties were hydroxyapatite $[Ca_{10}(PO_4)_6(OH)_2]$ and tricalcium phospate $[Ca_3(PO_4)_2]$. Their osteophilicity has been rationalized by their close similarity in chemical structure with the mineral phase of mammalian bone. More recently, this inventor has made the surprising discovery that chemical similarity with bone structure is not necessary for a mineral substance to exhibit osteophilic properties. Indeed, it has been found that calcite $[CaCO_3]$, dolomite $[CaMg(CO_3)_2]$ (See my copending U.S. patent application Ser. No. 251,225), and more recently the minerals fluorapatite, aragonite, magnesite, witherite and barite have been found to exhibit osteophilic properties. A number of researchers have sought to take advantage of in vivo chemical bonding of bone to bioactive mineral surfaces. See, for example, U.S. Pat. Nos. 3,787,900; 3,919,723;

4,168,326; 4,320,514; 4,366,188; 4,373,217; and 4,437,192.

The present invention is based on the discovery that certain organic polymers, that is, organic polymers bearing salt-forming oxyacid functional groups, exhibit an affinity toward developing bone tissue similar to that which has been observed for the above-mentioned inorganic mineral materials. The brittle nature of osteophilic minerals limits their usefulness to low stress applications. One such application is as a coating for porous-surfaced dental and orthopedic implants. It is known that pore sizes on the order of about 100–200 microns diameter are required for bony in growth into osteophobic materials. However, bone will grow into cracks and pores as small as 2 microns in diameter in osteophilic minerals. The pores of osteophobic metals, for example, have been coated with a thin layer of an osteophilic mineral to promote the rate of bony in growth. One serious problem related to the application of thin mineral coatings to porous metal surfaces is the lack of adhesion of such coatings to the metal substrate and the propensity for the minerals to dissolve in vivo when applied as thin films.

The present invention is based on the discovery that bone will deposit onto and chemically bond with organic polymeric materials having, at least on their bone contacting surfaces, covalently attached salt forming oxyacid functional groups. That discovery coupled with the inherent versatility of organic polymers for implant fabrication represents a significant advance in the art. Polymeric materials exhibit superior processability and mechanical properties. They can be extruded, molded, shaped and machined, or they can be applied, as a melt or dissolved in solution, to coat the surfaces of prosthetic devices constructed of other materials or material composites. Many biocompatible polymers in bulk form exhibit weight/strength properties (especially when reinforced with high tensile strength fibers) unmatched by the metal or metal/ceramic materials which have been used for construction of prosthetic devices. Still a further advantage of the use of biocompatible organic polymers for construction of orthopedic protheses is their chemical versatility. That is, implant devices constructed of or coated with biocompatible organic polymers can be surface modified by chemical treatment using a wide variety of reaction conditions to bear the desired surface-active oxyacid groups in accordance with this invention.

It is therefore an object of this invention to provide a method for promoting interfacial osteogenesis on an implant surface.

It is another object of this invention to provide a method for promoting bone in growth and bone adhesion to bone contacting surfaces of implanted prostheses.

Another object of this invention is to provide orthopedic prostheses having improved bone contacting surfaces comprised of a biocompatible organic polymer substituted with salt-forming oxyacid groups selected from the group consisting of the oxyacids of carbon, sulfur and phosphorus.

DETAILED DESCRIPTION OF THE INVENTION

The present invention provides a method for promoting bone in growth and bone adhesion to bone contacting surfaces of an orthopedic prosthesis. The method comprises forming the prosthesis so that at least the bone contacting surfaces thereof comprise a biocompatible organic polymer substituted with salt-forming oxyacid groups selected from the group consisting of the oxyacids of carbon, sulfur and phosphorous.

A prosthesis in accordance with this invention can assume one of a variety of alternate constructions. It can be formed using extrusion techniques, molded, shaped or machined either from a bulk oxyacid-substituted polymer or from a bulk polymer susceptible to chemical modification to form covalently bound surface oxyacid groups. Alternatively, the present prosthesis can be fabricated by coating a prosthesis core, constructed of an art-recognized biocompatible implant material or material composite, with oxyacid substituted organic polymers or polymers susceptible to chemical modification to form covalently bonded surface-active oxyacid groups. It is also within the scope of this invention to prepare prostheses in accordance with art-recognized prosthesis fabrication techniques employing organic polymeric components. Thus, the present prostheses can be constructed, for example, in accordance with any one of U.S. Pat. Nos. 3,314,420 (Apr. 8, 1967); 4,373,217 (Feb. 15, 1983); and 4,330,514 (May 18, 1982) using in place of the polymers disclosed in those patents, a bulk oxyacid-substituted polymer or a polymer susceptible to chemical modification to form covalently bound surface oxyacid groups. The disclosures of each of those U.S. patents are expressly incorporated herein by reference.

Illustrative of salt-forming oxyacid groups of carbon, sulfur and phosphorous are —COOH, —SO₃H, —O-SO₃H, —SO₂H, —OSO₂H, —PO(OH)₂, —P(OH)₂, —OPO(OH)₂, —OP(OH)₂ and —OPO₂HOPO(OH)₂. The polybasic phosphorous oxyacid groups canoptionally be in their corresponding partial ester forms represented by the formulas

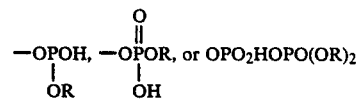

wherein R is allyl or lower alkyl, for example, methyl, ethyl, propyl or butyl.

From the standpoint of effectiveness for promoting interfacial osteogenesis and bone adhesion (chemical bonding to newly forming bone tissue) polymers substituted with phosphorous oxyacid groups are favored over those bearing carbon or sulfur oxyacid groups. Similarly polymer surfaces bearing carbon oxyacid groups, i.e. carboxylic acid or carboxylate, show greater efficacy in accordance with the present invention than do polymers substituted with sulfur oxyacid groups.

The biocompatible organic polymer itself can be any organic polymeric material which exhibits the requisite structural/biomechanical properties and in vivo chemical stability. It should be substantially free from chemical degradation in the presence of body tissue and body fluids. The biocompatible organic polymer can be a polymer substituted in bulk with the above-mentioned salt-forming oxyacid groups or the polymer can be substantially free of those groups in bulk but susceptible to surface modification by chemical treatment to contain said groups. Exemplary of biocompatible organic polymers which can be used in accordance with the present invention are polyolefins such as polyethylene and polypropylene, fluorinated polyolefins, polysulfones, polyvinylalcohols, polyamides, polydimethylsiloxanes, polyethyleneglycol terephthalates, polyurethanes, polyacrylonitriles, poly(methyl methacrylates), poly(2-hydroxyethyl methacrylate), polyvinylchlorides, polyvinylidene chlorides, polyethylene glycols, polyvinylpyrrolidones, polyetherurethanes, mixtures of those polymers and copolymers of copolymerizable monomers of said polymers.

Polymers bearing oxyacid groups in accordance with this invention are prepared using art-recognized polymerization techniques. Thus monomers bearing one or more of said oxyacid groups or functional group precursors to said oxyacid groups can be polymerized, or copolymerized with other monomers or block polymers to provide oxyacid substituted polymers or polymers having functional groups which upon chemical treatment can be converted to, or substituted by, the corresponding carbon, sulfur or phosphorous oxyacid groups. For example, a monomer bearing a hydrolyzable oxyacid ester group can be polymerized or copolymerized to form an organic polymer which is used either in bulk to form an orthopedic implant or to coat a prosthesis core in accordance with the present invention. Exposure of the polymer to hydrolytic conditions effects deesterification of surface-exposed ester groups to provide the corresponding oxyacid substituents. Alternatively surface oxyacid groups can be introduced by graft copolymerization of a monomer bearing the oxyacid group or a chemical precursor thereof onto the polymer surface of an implant. See, for example, U.S. Pat. No. 4,377,010 and the monomers described in Japanese Pat. No. 7143372. Another means of introducing a surface oxyacid groups, such as the sulfonic acid group, is by electrophilic substitution at surface accessible aromatic or olefinic sites in the polymer structure. Thus implants formed from (or coated with) polymers bearing aromatic groups can be sufonated with, for example, fuming sulfuric acid. Alternatively phosphorous or phosphonic acid groups can be introduced on such aromatic polymers by reaction with phosphorous trichloride in accordance with the disclosure of U.S. Pat. No. 2,911,378.

Nucleophilic substitution reactions can also be employed to surface modify organic polymers having displaceable substituent groups. For example, halogenated polymers can be reacted with strong carbon or oxygen nucleophiles bearing ester protected oxyacid groups to provide substitued polymers which upon hydrolytic deesterification yields a polymer surface having covalently bound oxyacid groups. The preparation of organic polymers bearing salt-forming oxyacid functional groups is well-known in the art particularly for the preparation of ion exchange resins—see U.S. Pat. Nos. 2,597,347; 2,340,111; 2,911,378; 3,252,921; and 3,717,594 and UK Pat. Nos. 726,918 and 973,971.

As mentioned above, the construction of orthopedic implants in accordance with the present invention is accomplished using one of several techniques. The implant can be formed, in bulk, from biocompatible polymer or copolymer bearing salt-forming oxyacid groups. Alternatively such an oxyacid-substituted polymer can be used to coat a prosthesis core. The core can be constructed of any material which is, preferably, itself biocompatible and which can provide the requisite structural/biomechanical properties to meet the "in use" demands for the prosthesis. Suitable core materials include metals, metal aloys, oxidic ceramic materials, biocompatible polymers, pyrolytic carbon and functional composites thereof. A prosthesis core can be coated either by spraying a solvent solution of the organic polymer on the core surface or by dipping the core into a polymer solution. The thickness of the coating is determined by the concentration of the polymer solvent solution and by the method and number of repetitions of application of that solution to the surface of the prosthesis core. Alternatively the core is coated by applying the polymer (containing oxyacid groups or chemically modifiable to contain oxyacid groups) as a melt.

In a preferred embodiment the prosthesis core has a porous surface corresponding to the bone contacting surfaces of the prosthesis itself. A thin (5-10 micron) coating of a biocompatible polymer bearing oxyacid groups or chemical group precursors to oxyacid groups can be applied by dipping the prosthesis core in a dilute solution of the polymer in a low-boiling organic solvent. The prosthesis is thereby fabricated to have a porous surface corresponding to that of the porous surface of the prosthesis core.

Alternatively, surface porosity can be introduced in the polymer coating or on the surface of a bulk polymer utilizing techniques well established in the polymer art. For example, a particulate material insoluble in the solvent used for the polymer itself, but soluble in a second solvent system, and having a particle size distribution corresponding to the desired pore size distribution, can be suspended in the polymer coating mixture or mixed with the bulk polymer itself. After the prosthesis core is coated with the polymer solution/particle suspension, the prosthesis is subjected to treatment in a second solvent system which dissolves the particulate material (now suspended in the polymer matrix) to leave a porous surface having pore sizes corresponding to the particle sizes of the suspended particulate material.

In a preferred embodiment of this invention the bone contacting surface of the prosthesis is a porous surface having pore sizes ranging from about 2 to about 500 microns, more preferably from about 10 to about 250 microns, and most preferably about 10 to about 150 microns. Bone in growth into surface pores as small as 2 microns has been observed on the osteophilic polymer surfaces in accordance with this invention.

Any of the above-described prosthesis fabrication techniques can be applied to the preparation of prostheses in accordanCe with the present invention requiring as the last step chemical treatment to effect substitution with or formation of the salt-forming oxyacid groups at the surface of the biocompatible polymer. Thus a prosthesis can be formed in bulk from a biocompatible organic polymer which is substantially free of oxyacid groups but which can be surface-treated to effect formation of or substitution with oxyacid groups in accordance with this invention. Similarly such a polymer can be applied as a coating to a prosthesis core as described above and thereafter surface modified, physically to effect surface porosity, and chemically to effect substitution with or formation of oxyacid substituents, on the polymer surface.

The oxyacid substituted biocompatible polymer comprising the bone contacting surfaces of the prosthesis of the present invention can be left in its acid form or preferably converted to and used in a biocompatible salt form, preferably its sodium, potassium or calcium salt form. The calcium salt form is most preferred.

The prostheses in accordance with the present invention exhibit excellent in vivo bone fixation. It is believed that this effect is due to formation of salt-type bridges between the oxyacid functional groups on the polymer and the carboxylated/sulfated biopolymers that comprise the organic phase of regeneating bone tissue.

Prior to surgical implantation the prostheses prepared in accordance with this invention are cleaned, sterilized and conditioned in accordance with conventional implant preparation techniques.

The present invention is further illustrated by the following examples, none of which are to be construed as limiting the invention in any respect.

EXAMPLE 1

The purpose of this experiment was to determine whether interfacial osteogenesis would occur onto materials with oxyacid surfaces. To establish the validity of the test method, known osteophobic materials were included as controls for comparison.

Materials

1. Polyacrylic Acid—cross linked with 8% divinyl benzene (carboxylic acid functionality). Supplied by Rohm and Haas, Philadelphia, Pa.—ref. U.S. Pat. Nos. 2,591,573; 2,591,574; 2,614,099; 2,629,710, 2,675,359.
2. Sulfonated Polystyrene—cross linked with 8% divinyl benzene (sulfonic acid functionality). Supplied by Rohm and Haas.
3. Polyethylene—Ultra high molecular weight, surgical grade.
4. Titanium—100% pure implant grade.

Methods

The above materials were implanted in the form of particles (0.5–1.0 mm diameter) into rat tibia using the following procedure.

The left tibia of each test animal was exposed using the technique detailed below in Example 2. A transcortical defect was made through the lateral aspect of the proximal surface of the tibia into the medullary canal using a dental burr. The medullary canal was reamed out to about 3 mm diameter. Particles of each material were packed into the defect in duplicate, two test animals per material. The incisions were closed and the animals were allowed to heal for 5 to 9 weeks. At the end of the test period the animals were sacrificed and the tibia excised. The implant sites were then processed histologically and observed using light microscopy.

Results

Histological examination of the implant sites revealed dramatic differences between the response of bone to the oxyacid containing polymers and its response to titanium and polyethylene.

In the cases of the polyethylene and titanium implants bone did not deposit directly onto the implant surfaces but remained separated from it by a layer of soft tissue of variable thickness. In the cases of the sulfonated polystyrene and cross linked poyacrylic acid, direct interfacial osteogenesis was observed over about 90% of the available surfaces. In some areas osteoblasts could be observed in the process of depositing bone onto the surfaces of these implants. There was no evidence of any soft tissue capsule separating these implants from the surrounding bone.

These results demonstrate the osteophilic nature of materials with oxyacid surfaces and redemonstrate the osteophobic nature of polyethylene and titanium surfaces.

EXAMPLE 2

The purpose of this experiment was to determine whether bone would chemically bond to materials with oxyacid surfaces. Again inert control materials were included in the study for comparisons.

Materials (1) Surface sulfonated polystyrene - sulfonic acid functionality. Solid blocks of polystyrene cross linked with 8% divinyl benzene were prepared. $4 \times 5 \times 1$ mm implants were cut from these blocks and polished to a smooth (600 grit) finish. The implants were sulfonated by exposure to fuming sulfuric acid for 1.5 and 15 minutes. This procedure is known to introduce sulfonic acid groups into the aromatic rings of the polymer chain. See for example British Pat. No. 973,971 and U.S. Pat. Nos. 3,717,594 and 3,252,921. The depth of sulfonation was measured by methylene blue dye adsorption to be about 10 microns in both cases.

(2) Surface hydrolysed polymethylacrylate-carboxylic acid functionality. Polymethylacrylate cross linked with 8% divinyl benzene was prepared using known methods (See U.S. Pat. Noa. 2,340,111 and 2,597,437). $4 \times 5 \times 1$ mm implants were cut and polished as above. Exposure to 10% NaOH for 120 minutes at room temperature resulted in the hydrolysis of the ester groups to a depth of about 5 microns as measured by methylene blue adsorption.

(3) Nonsulfonated polystyrene control—$4 \times 5 \times 1$ mm polystyrene implants were prepared as in (1) above but they were not sulfonated.

(4) Nonhydrolysed polymethylacrylate control—$4 \times 5 \times 1$ mm polymethylacrylate implants were prepared as above in (2) but not hydrolysed.

(5) Titanium control—medical grade titanium was cut into $4 \times 5 \times 1$ mm implants and polished as above.

(6) Polymethylmethacrylate control—commercial grade polymethylmethacrylate was cut into $4 \times 5 \times 1$ mm implants and polished as above.

(7) Polyethylene—ultra high molecular weight medical grade polyethylene was cut into $4 \times 5 \times 1$ mm implants.

Methods

The presence or absence of bony adhesion to the test and control materials was determined in part by the known mini pushout test. This test employs the following procedure. Male Sprague-Dawley rats in the 150 to 250 gram range are used as the test animal. After anesthetizing the animal, an incision is made on the anterior surface of the left hind leg from the knee to midway down the tibia. The proximal aspect of the tibia is then exposed. A high speed dental drill is then used to form a slot wholly through the anterior end of the tibia. The $4 \times 5 \times 1$ mm implants are inserted into the defects with their long axis perpendicular to the tibia. The relative dimensions of the implant and the tibia are such that the implant protrudes slightly on either side of the tibia after implantation. The incision is then closed and the animal allowed to heal. Testing for bonding with bone after 5 to 7 weeks provide a reliable test for bony adhesion. After sacrifice, the test tibia are excised from each animal and cleaned of soft tissues. The area directly over the exposed ends of the implant is then cleared of any bony overgrowth to prevent mechanical interlock.

The mechanical integrity of the bone implant bone is then tested using modified sponge forceps which apply a 22 newton pushout load on the implant. If the implant remains firm under the applied load, then it is deemed to have passed the mini pushout test for bonding. If any perceptible movement is observed between the bone and the implant, then it is considered to have failed this test for bonding.

Implants that failed the mini pushout test were placed into buffered formalin and observed histologically. Implants passing this test for bonding were then subjected to a further test of their bonding with bone.

This second test consisted of subjecting the bone implant interface to increasing tensile loading until failure occurred. Subsequent gross and microscopic examination of the fracture surface revealed the locus of failure.

The observation of an adherent layer of bone fragment on the implant surface or of implant on the bone surface indicates an adhesive bone strength greater than the bulk strength of the bone or the implant respectively. This cohesive mode of failure is indicative of direct chemical bonding. Where clean interfacial separation occurs the failure mode is adhesive in nature.

Results

The control materials consisting of nonhydrolysed polymethylacrylate, nonsulfonated polystyrene, polymethylmethacrylate, titanium and polyethylene all failed the mini pushout test after 5 weeks Histological examinations of the implant-tissue interfaces revealed a similar tissue response in all cases. Direct bone-implant contact was minimal (less than 10% of the available implant surfaces). Over 90% of the available implant surfaces were separated from the surrounding bone by a layer of soft tissue at least 10 microns in thickness. No osteoblastic activity was seen next to the implant surface.

The test materials consisting of polystyrene sulfonated for 1.5 and 15 minutes and the surface hydrolysed polymethylacrylate all passed the mini pushout test for bonding after 5 weeks. These implants were then subjected to the failure locus described above. Subsequent histological observation of the implantation sites revealed direct bone-implant contact in over 95% of the available implant surface in all of these cases. Close examination of the bone-implant interfaces revealed fragments of bone adhering to the implants over about 50% of the surface and fragments of implant stuck to bone over about 45% of the fracture surface. Clean interfacial separation was not observed with these implants.

Discussion

The fact that bone will interface with and adhere to surface sulfonated polystyrene and surface hydrolysed polymethylacrylate is especially interesting when compared to the fact that it does not deposit onto or bond with nonsulfonated polystyrene or nonhydrolysed polymethylacrylate. Since the only difference between these materials is the presence of oxyacid groups at the implant surface, it is clear that the presence of these groups is the active agent in conferring the osteophilic response. The mechanism of bond formation is believed to involve the formation of salt-type bridges between the oxyacids groups on the polymer surface and similar groups present in the structural components of healing bone.

It is now believed that any polymeric substrate containing these osteophilic groups at least on their bone bonding surfaces would be expected to serve as a satisfactory substrate for interfacial osteogenesis and promote direct bony adhesion.

EXAMPLE 3

A high modulus aromatic polysulfone is prepared by reacting p,p'-dichlorodiphenyl sulfone and the disodium salt of bisphenol A. A bone prosthesis is molded from the polymer. The surfaces of the prosthesis intended for contact with living bone are treated for 10 minutes at room temperature with fuming sulfuric acid. The implant is washed with distilled water and treated with an aqueous solution of sodium bicarbonate. The bone contacting polymer surface of the implant are found to be substituted with sodium sulfonate groups. The bone contacting surfaces exhibit high affinity for developing bone tissue.

EXAMPLE 4

The same procedure is followed as in Example 3 except that the bone prosthesis molded from the aromatic polysulfone is treated with phosphorous trichloride in the presence of aluminum chloride in accordance with the procedure described in U.S. Pat. No. 2,911,378 and British Pat. No. 726,918 to effect substitution at and near the polymer surface with covalently bonded phosphonic acid groups and as demonstrated by methylene blue staining. The bone contacting surfaces exhibit high affinity for developing bone tissue.

EXAMPLE 5

A bone prosthesis is molded from polystyrene cross linked with 8% divinyl benzene. The surfaces of the prosthesis intended for contact with living bone are treated for 10 minutes at room temperature with fuming sulfuric acid. The implant is washed with distilled water. Staining with methylene blue dye demonstrates the introduction of sulfonic acid groups on the exposed polymer surfaces The prosthesis is suspended in calcium hydroxide solution for a period of 1 hour at room temperature and washed with distilled water. The bone contacting surfaces are found to be substituted with calcium sulfonate groups and exhibit high affinity for developing bone tissue.

I claim:

1. A method for promoting deposition and adhesion of developing bone tissue onto a surface of an implanted prosthesis and for promoting growth of developing bone tissue into any pores in said prosthesis surface as small as 2 microns in diameter which method comprises selecting the prosthesis so that at least the prosthesis surface intended for contact with developing bone tissue comprises a biocompatible organic polymer substituted with salt-forming oxyacid groups selected from the group consisting of the oxyacids of carbon, sulfur and phosphorus, and implanting said prosthesis so that said surface is accessible to developing bone tissue whereby the deposition and adhesion of developing bone tissue to the surface of the implanted prosthesis operates to secure the implanted prosthesis in a fixed position relative to adjacent bone tissue.

2. The method of claim 1 wherein the oxyacid groups are converted to a biocompatible salt form.

3. The method of claim 2 wherein the oxyacid groups are converted to their corresponding alkali metal salts.

4. The method of claim 2 wherein the oxyacid groups are converted to a corresponding salt form selected from the group consisting of potassium, sodium and calcium salts.

5. The method of claim 1 wherein the biocompatible organic polymer is selected from the group consisting of polyolefins, fluorinated polyolefins, polysulfones, polyvinylalcohols, polyamides, polydimethylsiloxanes, polyethyleneglycol terephthalates, polyurethanes, polyacrylonitriles, poly(methyl methacrylates), poly(2-hydroxyethyl methacrylate), polyvinylchlorides, polyvinylindene chlorides, polyethylene glycols, poylvinylpyrrolidones, poyetherurethanes, mixtures of those polymers and copolymers of copolymerizable monomers of said polymers.

6. The method of claim 1 wherein the prosthesis is formed by coating a biocompatible prosthesis core with the oxyacid substituted biocompatible organic polymer.

7. The method of claim 6 wherein the prosthesis core is constructed of a material selected from the group consisting of metals, metal alloys, oxidic ceramic materials, biocompatible polymers, pyrolytic carbon, and composites thereof.

8. The method of claim 7 wherein the prosthesis core has porous surfaces corresponding to the bone tissue contacting surfaces of the prosthesis.

9. The method of claim 8 wherein the bone tissue contacting surfaces of the prosthesis comprise a porous surface having pore sizes ranging from about 2 to about 500 microns.

10. The method of claim 1 wherein the selected prosthesis is formed by coating a prosthesis core with a biocompatible organic polymer substantially free of salt-forming oxyacid groups and chemically treating the coated prosthesis core to effect substitution with or formation of the salt-forming oxyacid groups at least at the surface of the biocompatible polymer coating.

11. The method of claim 10 wherein the oxyacid groups are formed at the surface of the biocompatible organic polymer coating by chemical conditions effecting a reaction selected from the group consisting of graft copolymerization, deesterification, electrophilic substitution and nucleophilic substitution.

12. The method of claim 1 wherein the selected prosthesis is formed from an oxyacid substituted biocompatible organic polymer.

13. The method of claim 1 wherein the selected prosthesis is formed of a biocompatible organic polymer substantially free of salt-forming oxyacid groups and is treated chemically to effect substitution with or formation of the salt-forming oxyacid groups at the surface of the biocompatible polymer.

14. In a prosthesis having a porous surface adapted for prosthesis-securing engagement with ingrowing bone tissue, the improvement consisting essentially of forming said porous surface to comprise a biocompatible organic polymer substituted with salt-forming oxyacid groups selected from the group consisting of —$SO_3H$, —$OSO_3H$, and —$SO_2H$.

15. The improvement of claim 14 wherein the oxyacid groups are in a biocompatible salt form.

16. The improvement of claim 15 wherein the oxyacid groups are in the form of their corresponding salts selected from the group consisting of potassium, sodium and calcium salts.

17. The improvement of claim 14 wherein the biocompatible organic polymer is selected from the group consisting of polyolefins, fluorinated polyolefins, polysulfones, polyvinylalcohols, polyamides, polydimethylsiloxanes, polyethyleneglycol terephthalates, polyurethanes, polyacrylonitriles, poly(methyl methacrylates), poly(2-hydroxyethyl methacrylate), polyvinylchlorides, polyvinylidene chlorides, polyethylene glycols, polyvinylpyrrolidones, polyetherurethanes, mixtures of those polymers and copolymers of copolymerizable monomers of said polymers.

18. The improvement of claim 14 where the porous surface is formed as a coating of an oxyacid-substituted biocompatible organic polymer on a biocompatible prosthesis core.

19. The improvement of claim 18 wherein the prosthesis core is formed from a material selected from the group consisting of metal, metal alloys, oxidic ceramic material, biocompatible organic polymers, pyrolytic carbon and composites thereof.

20. The improvement of claim 14 wherein the porous surface has pore sizes ranging from about 2 to about 500 microns.

21. The improvement of claim 19 wherein the prosthesis core has a porous surface corresponding to the porous surface of the prosthesis.

22. The improvement of claim 21 wherein the prosthesis core is coated with a biocompatible organic polymer substantially free of salt-forming oxyacid groups and thereafter the coated core is treated chemically to effect formation of or substiution with the salt-forming oxyacid groups at the surface of the biocompatible polymer.

23. The improvement of claim 14 wherein the prosthesis is formed from a biocompatible polymer substituted with salt-forming oxyacid groups.

24. The improvement of claim 14 wherein the prosthesis is formed from a biocompatible organic polymer substantially free of salt-forming oxyacid groups and thereafter treated chemically to effect surface substitution with or formation of the salt-forming oxyacid groups at least at the surface of the biocompatible organic polymer.

25. A method for immobilizing bone prosthesis having a surface comprising a biocompatible organic polymer substituted with salt-forming oxyacid groups selected from the group consisting of the oxyacids of carbon, sulfur and phosphorus, said method consisting essentially of the step of implanting the prosthesis so that at least a portion of its surface will come into contact with developing bone tissue and promote the formation of prosthesis-immobilizing chemical bonds between at least a portion of said salt-forming oxyacid groups and the developing bone tissue.

26. The method of claim 25 wherein the surface of the bone prosthesis has pores ranging in size from about 2 microns to about 500 microns and wherein said prosthesis-immobilizing chemical bonds are formed in said pores.

27. The method of claim 25 wherein the salt-forming oxyacid group is —COOH.

28. The method of claim 25 wherein the salt-forming oxyacid group is an oxyacid of phosphorus.

29. The method of claim 25 wherein the salt-forming oxyacid group is an oxyacid of sulfur.

* * * * *